US009241811B2

(12) United States Patent
Davenport et al.

(10) Patent No.: US 9,241,811 B2
(45) Date of Patent: Jan. 26, 2016

(54) METHOD AND APPARATUS FOR IMPLANTING A PROSTHESIS

(75) Inventors: Austen Davenport, Columbia City, IN (US); Aaron P. Smith, Warsaw, IN (US); Tyler D. Witt, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 531 days.

(21) Appl. No.: 13/619,111

(22) Filed: Sep. 14, 2012

(65) Prior Publication Data

US 2014/0081282 A1   Mar. 20, 2014

(51) Int. Cl.
*A61F 2/30* (2006.01)
*A61F 2/46* (2006.01)

(52) U.S. Cl.
CPC ............ *A61F 2/4603* (2013.01); *A61F 2/4609* (2013.01); *A61F 2002/30426* (2013.01); *A61F 2002/4624* (2013.01); *A61F 2002/4629* (2013.01); *A61F 2002/4681* (2013.01)

(58) Field of Classification Search
CPC ............... A61F 2/4603; A61F 2/4609; A61F 2002/30426
USPC ........... 606/89, 96, 99; 403/21, 109.2, 109.3, 403/109.6, 109.8, 348, 349, 353, 377; 285/402
See application file for complete search history.

(56) References Cited

U.S. PATENT DOCUMENTS

| | | | | |
|---|---|---|---|---|
| 788,200 | A | * | 4/1905 | Pinch ............................ 126/318 |
| 1,033,187 | A | * | 7/1912 | Metzger ......................... 285/87 |
| 3,661,411 | A | * | 5/1972 | Flick ............................. 403/348 |
| 3,859,910 | A | * | 1/1975 | Swanson, Jr. ................. 100/100 |
| 4,023,572 | A | | 5/1977 | Weigand et al. |
| 4,142,809 | A | * | 3/1979 | Shell ............................. 403/201 |
| 4,306,743 | A | * | 12/1981 | Hinshaw et al. .............. 285/260 |
| 4,344,190 | A | | 8/1982 | Lee et al. |
| 4,697,584 | A | | 10/1987 | Haynes |
| 4,716,894 | A | | 1/1988 | Lazzeri et al. |
| 4,982,581 | A | * | 1/1991 | Furuyama ...................... 63/29.1 |
| 5,092,891 | A | | 3/1992 | Kummer et al. |
| 5,236,433 | A | | 8/1993 | Salyer |
| 5,683,399 | A | | 11/1997 | Jones |
| 5,954,727 | A | | 9/1999 | Collazo |

(Continued)

FOREIGN PATENT DOCUMENTS

DE   19824328 C1   3/2000
DE   10148022 A1   5/2003

(Continued)

OTHER PUBLICATIONS

International Search Report and Written Opinion mailed Oct. 30, 2013 for PCT/US2013/058442 (filed Sep. 6, 2013), which claims the benefit of U.S. Appl. No. 13/619,111, filed Sep. 14, 2012.

(Continued)

*Primary Examiner* — David Bates

(74) *Attorney, Agent, or Firm* — Schwegman Lundberg & Woessner, P.A.

(57) ABSTRACT

Disclosed is a system for engaging a prosthesis and for implanting the same. The system can include a component or plurality of components to engage an acetabular prosthesis in both rotational and axial fixation. A method of using the insertion assembly is also disclosed. In addition, a method of assembling, disassembling, and cleaning the insertion assembly is disclosed.

27 Claims, 9 Drawing Sheets

(56) References Cited

U.S. PATENT DOCUMENTS

| | | | |
|---|---|---|---|
| 6,126,359 A * | 10/2000 | Dittrich et al. | 403/349 |
| 6,179,842 B1 | 1/2001 | Spotorno et al. | |
| 6,299,616 B1 * | 10/2001 | Beger | 606/86 R |
| 6,626,913 B1 | 9/2003 | McKinnon et al. | |
| 7,296,804 B2 | 11/2007 | Lechot et al. | |
| 7,396,357 B2 | 7/2008 | Tornier et al. | |
| 7,621,921 B2 | 11/2009 | Parker | |
| 7,657,960 B2 * | 2/2010 | Umbrell | 15/230.19 |
| 7,682,363 B2 | 3/2010 | Burgi et al. | |
| 7,998,147 B2 | 8/2011 | Santarella et al. | |
| 2005/0038443 A1 | 2/2005 | Hedley et al. | |
| 2009/0112219 A1 | 4/2009 | Daniels et al. | |
| 2009/0112220 A1 | 4/2009 | Kraus | |
| 2010/0049257 A1 | 2/2010 | Parker | |
| 2012/0232601 A1 * | 9/2012 | Chabansky et al. | 606/86 A |
| 2014/0154004 A1 * | 6/2014 | Agate | 403/349 |

FOREIGN PATENT DOCUMENTS

| | | |
|---|---|---|
| EP | 1813229 A1 | 8/2007 |
| EP | 2345392 A1 | 7/2011 |
| GB | 2243890 A * | 8/1990 |
| WO | WO-03065941 A1 | 8/2003 |

OTHER PUBLICATIONS

International Preliminary Report on Patentability and Written Opinion mailed Mar. 26, 2015 for PCT/US2013/058442 (filed Sep. 6, 2013;), which claims the benefit of U.S. Appl. No. 13/619,111, filed Sep. 14, 2012.

* cited by examiner

METHOD AND APPARATUS FOR IMPLANTING A PROSTHESIS

FIELD

The subject disclosure relates to an instrument and method for positioning a prosthesis, and particularly to a method and apparatus for engaging and disengaging from an acetabular prosthesis.

BACKGROUND

This section provides background information related to the present disclosure which is not necessarily prior art.

In performing a procedure on a patient, a prosthesis can be used to replace or augment a natural anatomical feature. For example, due to age, injury, disease, or other causes, a portion of the anatomy may need to be replaced or resurfaced. Examples include replacing an acetabulum on a patient either in conjunction with or separate from replacing or resurfacing a femoral head. An acetabular prosthesis is generally positioned within a prepared acetabulum.

Positioning an acetabular prosthesis within a prepared acetabulum can include various dexterous movements. The acetabular prosthesis is generally positioned within the acetabulum in a selected alignment and position. The alignment of the acetabular prosthesis can include rotational positioning that is generally selected to be relative to the natural anatomy. The prosthesis includes a central axis that must be aligned and positioned or is selected to be aligned and positioned with a portion of the natural anatomy. In positioning the acetabular prosthesis in the selected position, both position and axial alignment can be selected.

When positioning, the acetabular prosthesis also needs to be engaged into the acetabulum with a selected force to ensure proper seating and positioning of the acetabular prosthesis. Accordingly, positioning the acetabular prosthesis generally requires dexterity on the part of the user, such as a surgeon, to position the acetabular prosthesis appropriately in a patient's anatomy. Then a force is applied to assist in fixing the prosthesis in the pelvis.

SUMMARY

An instrument can include a threaded rod that can engage a prosthesis, such as an acetabular prosthesis. The threaded rod can be positioned inside of a through-bore in a handle member and engage a portion of the handle member to allow the acetabular prosthesis to be brought into contact with the handle member. Interconnection of the handle member and the threaded rod can hold the prosthesis both linearly and rotationally relative to an insertion assembly for positioning an acetabular prosthesis with adaptation. In other words, the connection of the threaded rod, the prosthesis, and the handle member can hold the prosthesis from axial movement relative to the handle member. Further, the prosthesis can be rotationally fixed relative to the handle member.

In a method of using the instrument, the threaded rod can engage the acetabular prosthesis at a first end and a second end can be received within the handle member to engage a mechanism therein to fix or move the rod assembly and the connected prosthesis into contact with the handle assembly. The interconnected prosthesis and handle assembly can then be used to position the prosthesis into a prepared acetabulum. The method can then reverse to allow for disconnection of the acetabular prosthesis by disengaging the threaded rod from the acetabular prosthesis and then disassembling the threaded rod from the handle. A procedure can then be completed by implanting additional components, such as a femoral component or a liner, and closing a patient.

A system to implant a prosthesis into a subject is disclosed, according to various embodiments. The system can include a handle member extending from a first end to a second end and defining a through-bore through at least a portion of the handle member and a threaded member extending from a first end to a second end, the threaded member having threads formed at the first end to threadably engage the prosthesis and a slotted region at the second end. A projection can be provided to extend into the through-bore formed in the handle member to engage the slotted region to hold the threaded member in the handle member. The slotted region includes a first portion and a second portion separate from the first portion that includes a complete groove extending about the threaded member.

According to various embodiments, a system to implant a prosthesis into a subject is disclosed. The system can include a handle member extending from a first end to a second end and defining a through-bore through at least a portion of the handle member; and a threaded member extending from a first end to a second end. The threaded member can include a thread formed at the first end to threadably engage the prosthesis. The threaded member can further include a slotted region at the second end including a first portion that is discontinuous about the threaded member formed by at least a first slot wall and a second slot wall, wherein a first opening is formed through a first slot wall and a second opening through the second slot wall with a short groove defined between the first slot wall and the second slot wall extending a part of a distance around the threaded member between the first opening and the second opening and a second portion that includes a long groove extending completely about the threaded member. The system can also include a projection member extending into the through-bore formed in the handle member to engage the slotted region to hold the threaded member in the handle member. The projection is operable to engage both the first portion that is discontinuous to limit a rotation of the threaded member within the handle member and the second portion that includes the long groove to allow a complete rotation of the threaded member within the handle member.

According to various embodiments, a method of implanting a prosthesis into a subject is disclosed. The method can include providing a handle member extending from a first handle end to a second handle end and having a through-bore through at least a portion of the handle member and providing a threaded member extending from a first threaded member end to a slotted region at a second threaded member end for positioning into the through-bore. The threaded member can include a thread formed at the first threaded member end to threadably engage the prosthesis. The threaded member can further include a slotted region at the second threaded member end including a first portion that is discontinuous about the threaded member formed by at least a first slot wall and a second slot wall, wherein a first opening is formed through the first slot wall and a second opening is formed through the second slot wall with a short groove defined between the first slot wall and the second slot wall extending at least a part of a distance around the threaded member between the first opening and the second opening and a second portion that includes a long groove extending completely about the threaded member. The method can further include providing a projection member extending into the through-bore to engage the slotted region to hold the threaded member in the handle member. The projection can be operable to engage the first portion direct movement of the threaded member within the handle member and engage the second portion that includes the long groove to allow a complete rotation of the threaded member within the handle member.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
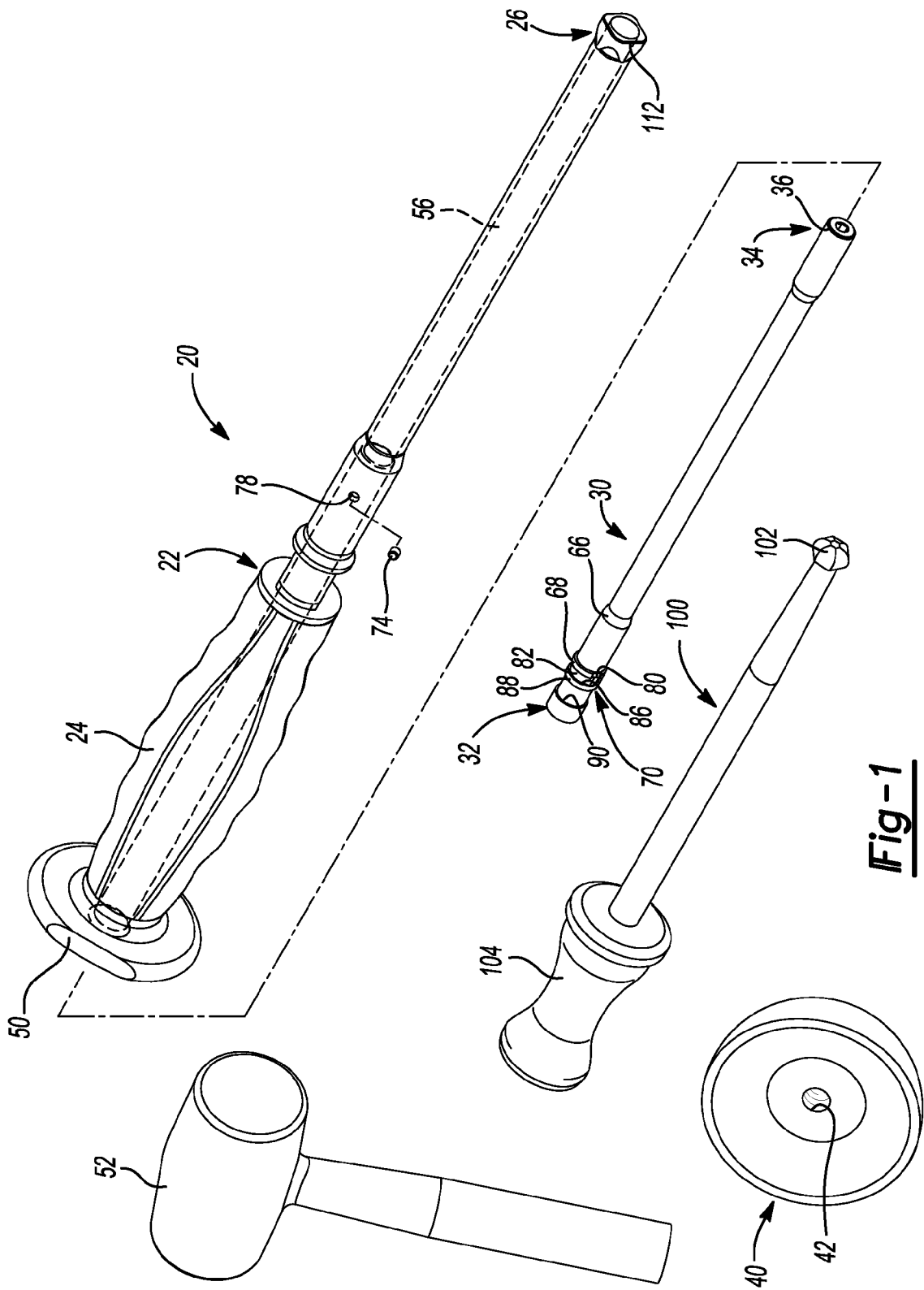
FIG. 1 is an exploded view of an insertion assembly, accordingly to various embodiments.

Example embodiments will now be described more fully with reference to the accompanying drawings.

With reference to FIGS. 1, 2, 3, 4A, and 4B, an inserter assembly 20 is illustrated. The inserter assembly 20 can generally include a handle or graspable member 22 including a graspable portion 24 near a first end and a prosthesis engaging region 26 at a second end. Generally, the prosthesis engaging end 26 can include a selected or keyed shape to assist in resisting rotation of a prosthesis relative to the graspable member 22, as discussed further herein. The keyed shape can include generally non-circular shapes, such as a square or other shape with at least one flat side.

The insertion assembly 20 also includes a threaded rod member 30 that extends from a first end 32 to a second end 34. The second end 34 can include an external thread 36 that can engage a prosthesis, such as an acetabular prosthesis 40, in an internally threaded bore 42. The threaded bore 42 can include a through-bore or a blind bore formed into the acetabular prosthesis 40. Additionally, the threaded rod 30 can engage an internal surface of the acetabular prosthesis 40 to allow for manipulation of the acetabular prosthesis 40, particularly when the threaded rod 30 is assembled into the graspable or handle member 22, as discussed further herein. The acetabular prosthesis 40 can further include a depression or portion to engage the keyed shape of the handle member 22. Also, it is understood, that any other appropriate prosthesis or member can engage the handle member; other examples include a femoral prosthesis or a humeral prostheses. Also, non-medical members can be engaged, such as a machine part that is to be held relative to an tool for assembly or use.

The handle member 22 can further include an impaction end or portion 50 that can be impacted with a mallet 52 or other appropriate surgical impaction tool. As discussed further herein, the prosthesis 40 can be engaged relative to the handle member 22 and the impaction tool 52 can be used to impact the acetabular prosthesis 40. Further, the graspable portion 24 can be formed of an appropriate material to assist grasping by a user. For example, the graspable portion 24 can be formed of or covered with a soft or malleable material, such as a natural or synthetic rubber. In addition, the graspable portion can include ridges, knurls, or other detents or shapes to assist in grasping the graspable portion 24.

The handle member 22 can define a through-bore or cannula 56. The bore 56 can extend through the entirety of the handle member 22 such that the threaded rod 30 can extend into the handle member 22 through the cannula 56, as discussed further herein. The threaded rod 30 can be inserted into the handle member 22, generally, through the end including the impaction portion 50. The threaded rod 30 can then be manipulated to engage the prosthesis 40.

Figure 2:
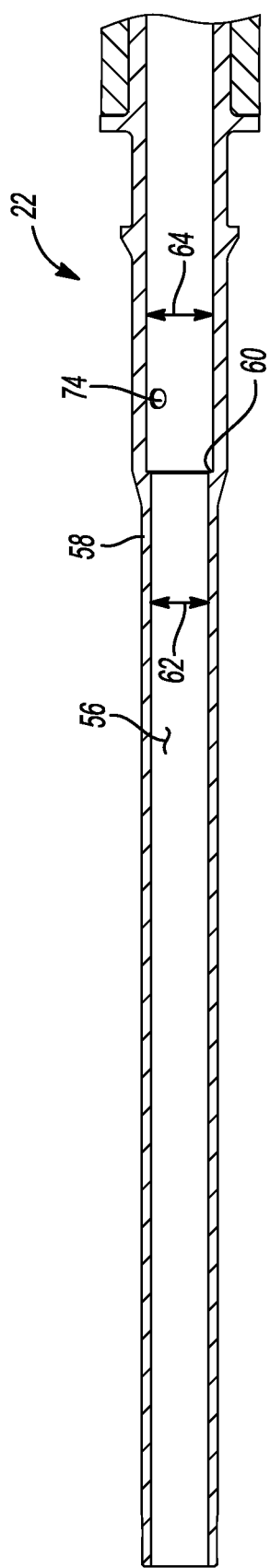
FIG. 2 is a detailed cross-sectional view of the handle member of the insert assembly according to FIG. 1.
Figure 3:
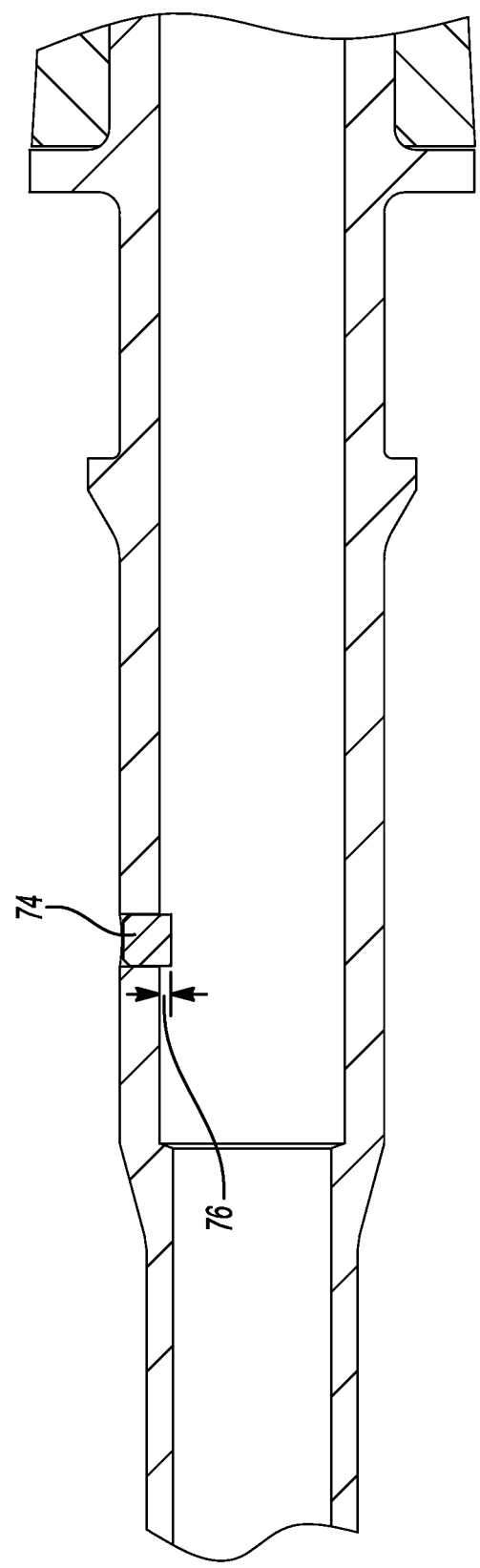
FIG. 3 is a detailed cross-sectional view of a different prospective of the handle member of the insertion assembly of FIG. 1.
Figure 4A:
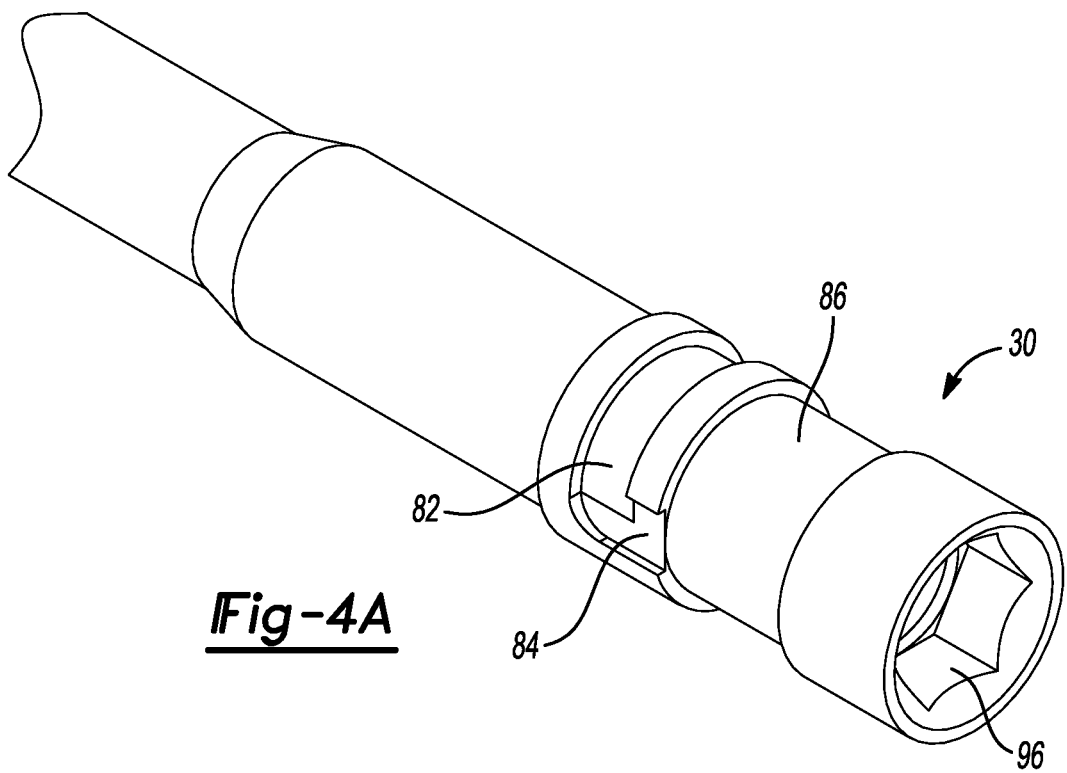
FIG. 4A is a detailed perspective view of a slotted portion of the threaded rod of the insertion assembly according to FIG. 1.
Figure 4B:
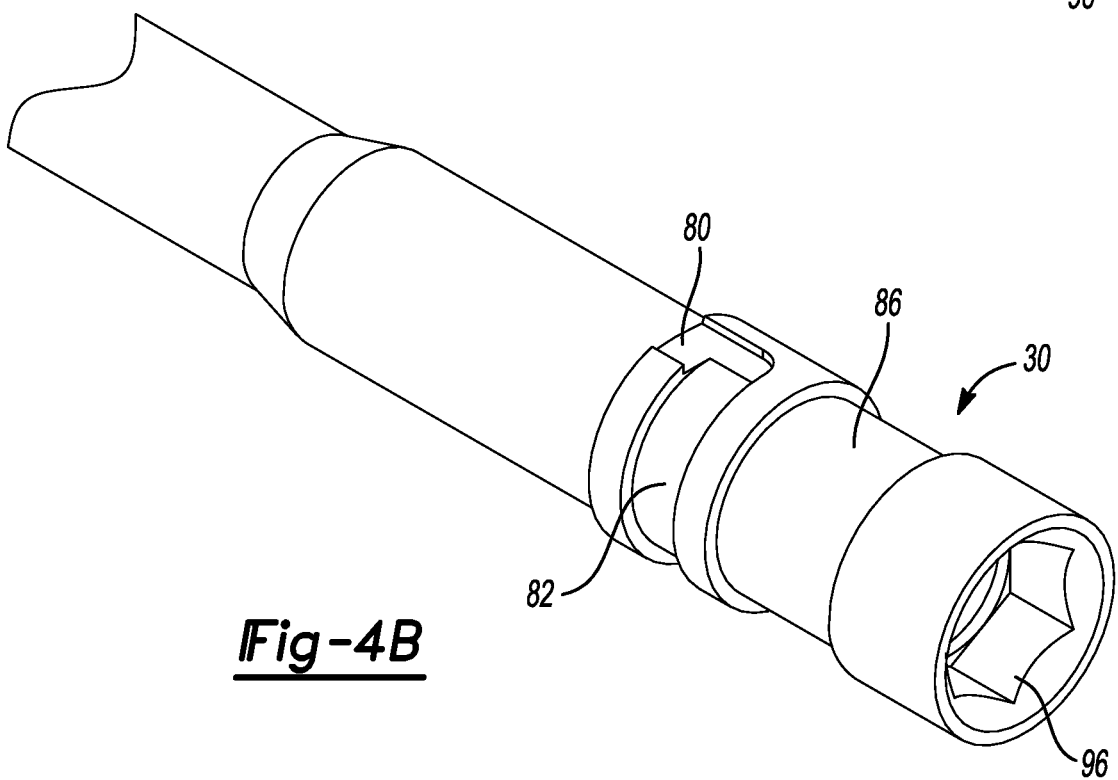
FIG. 4B is an alternative perspective view of the slotted end of the threaded rod of the insertion assembly according to FIG. 1.

With particular reference to FIGS. 2 and 3, and continued reference to FIG. 1, the cannula 56 through the handle member 22 can be defined or formed through an outer wall 58 of the handle member 22. The wall 58 with the handle member 22 can further include at least a shoulder or protrusion 60 that extends into the cannula. The shoulder can be formed at a transition in internal diameters of the cannula 56. The cannula 56 can include a first internal diameter 62 near the prosthesis engaging end 26 and a second greater diameter 64 closer to the impaction portion 50. The shoulder 60 can engage a complimentary or extending shoulder 66 of a bottom surface or slot wall 68 of a slot region or portion 70 of the threaded rod 30, as discussed further herein.

Additionally, a protruding member or protrusion 74 can extend a distance 76 into the internal diameter 64 of the cannula 56. The protrusion 74 can extend the distance 76 into the cannula 56 to engage the slotted region 70 of the threaded rod 30. The protrusion 74 can be formed as a separate member that is inserted into a passage or bore 78 of the handle member 22. It is understood, however, that the protruding member 74 can also be formed integrally with the handle member 22 as a single piece. Also, the distance 76 that the protrusion extends can be selected based on an amount of resist selected to maintain the threaded rod 30 in the handle member 22.

The threaded rod 30 that includes the slot region 70 can generally include a double-"J" or double-bayonet slot configuration. In the double-J slot configuration, a first entry passage or opening 80 is formed through the slot wall 68 that leads into a first circumferential groove or path 82. The slot wall 68 can also be referred to as a slot wall and the first groove 82 can be a short or non-complete circumferential groove defined at least in part by the slot wall 68. The short groove 82 is a partial circumferential passage.

The short groove 82 passes at least a certain distance around the threaded rod 30 to a second passage or opening 84. Generally, however, the short groove 82 does not circumscribe the threaded rod 30. A second passage or opening 84 can open from the short groove 82 and into a long groove 86. The long groove or complete path 86 is a complete circumferential passage or path that surrounds the entire circumference of the threaded rod 30. The complete path 86 is defined as an area of clearance or uninterrupted area between a second slot region ledge 88 and a third or proximal ledge 90. The second opening is through the second slot wall 88. It is understood, however, that the short groove 82 can be a complete groove (i.e. a groove that completely circumscribes the threaded rod 30) as long as the first opening 80 is not aligned with the second opening 84.

As discussed further herein, the projection member 74 can pass through the slot region 70 by passing through the first opening 80, moving into and through the short groove 82, and then through the second opening 84 into the complete circumferential area or passage 86. As discussed further herein, the threaded rod 30 can be rotated completely, at least once and generally multiple times, when the projection 74 is positioned in and riding within the complete circumferential passage 86. The double-"J" slot configuration is to provide a serpentine path for the projection 74 such that the threaded rod 30 can be efficiently maintained within the handle member 22. Thus, as discussed above, the short groove 82 can be provided to circumscribe the threaded rod 30 so long as the two openings 80, 84 are not aligned along the length of the threaded rod 30. When the openings 80, 84 are not aligned then the threaded rod 30 must be rotated for the threaded rod 30 to move relative to the projection 74.

A tool engaging region or portion 96 can be defined by an end of the threaded rod 30 to manipulate and twist the threaded rod 30 relative to the handle member 22. An insertion or driver tool 100 that engages the tool engagement region 96 can be formed to pass through at least a portion of the cannula 56 to engage the threaded rod 30 when it is positioned within the cannula 56. The driving tool 100 can include a driving tip 102 that engages the tool engaging region 96 of the threaded rod 30. The driving tip 102 can be any appropriate shape, such as a hex-drive, cruciform, or other driving shape. As illustrated the driving tip 102 can be a rounded or curved hex shaped drive. The driver tool 100 can include a handle 104 to be grasped by a user to rotate the driver instrument 100 to rotate the threaded rod 30.

Figure 5:
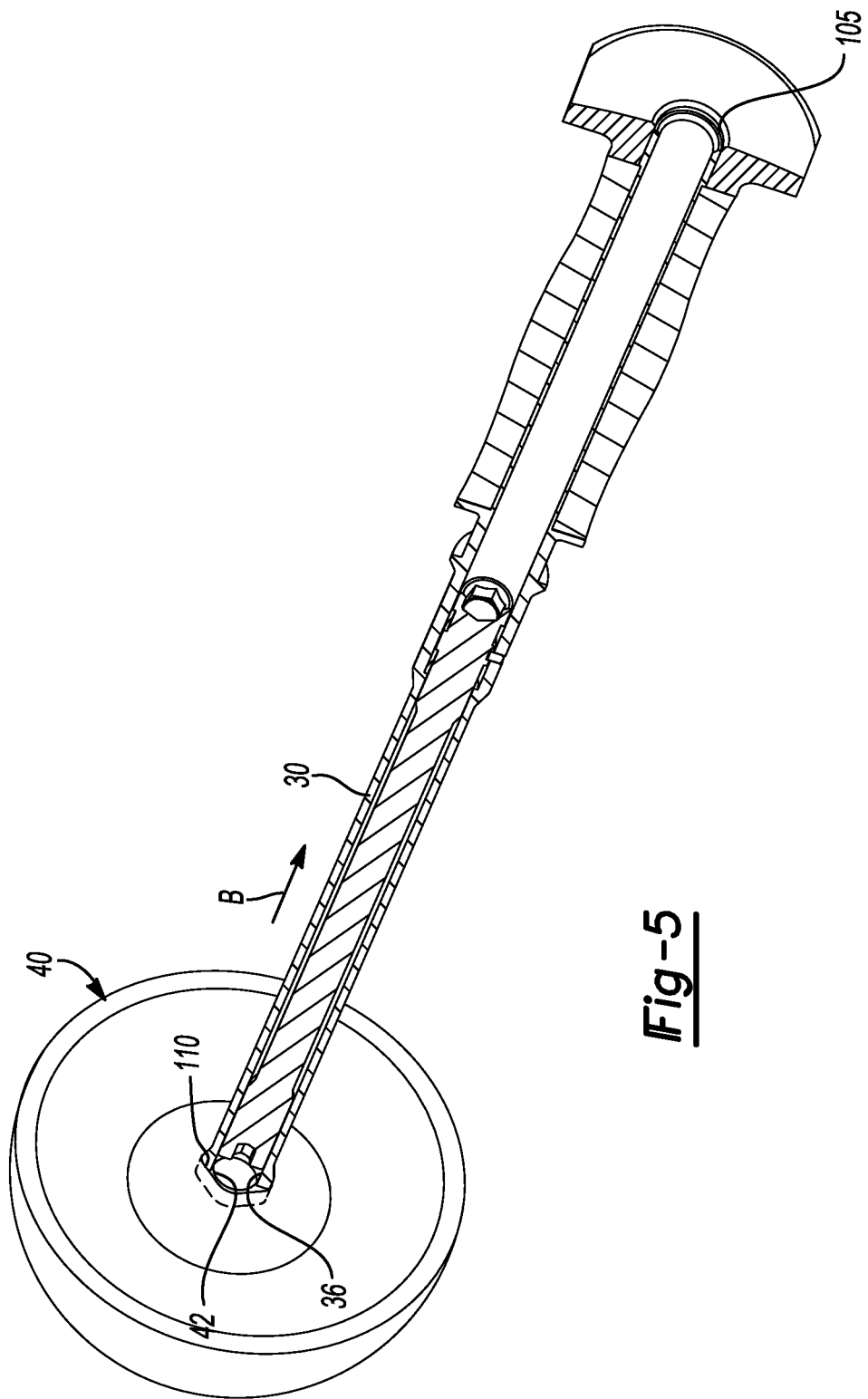
FIG. 5 is a cross-sectional perspective view of the insertion assembly of FIG. 1.
Figure 6:
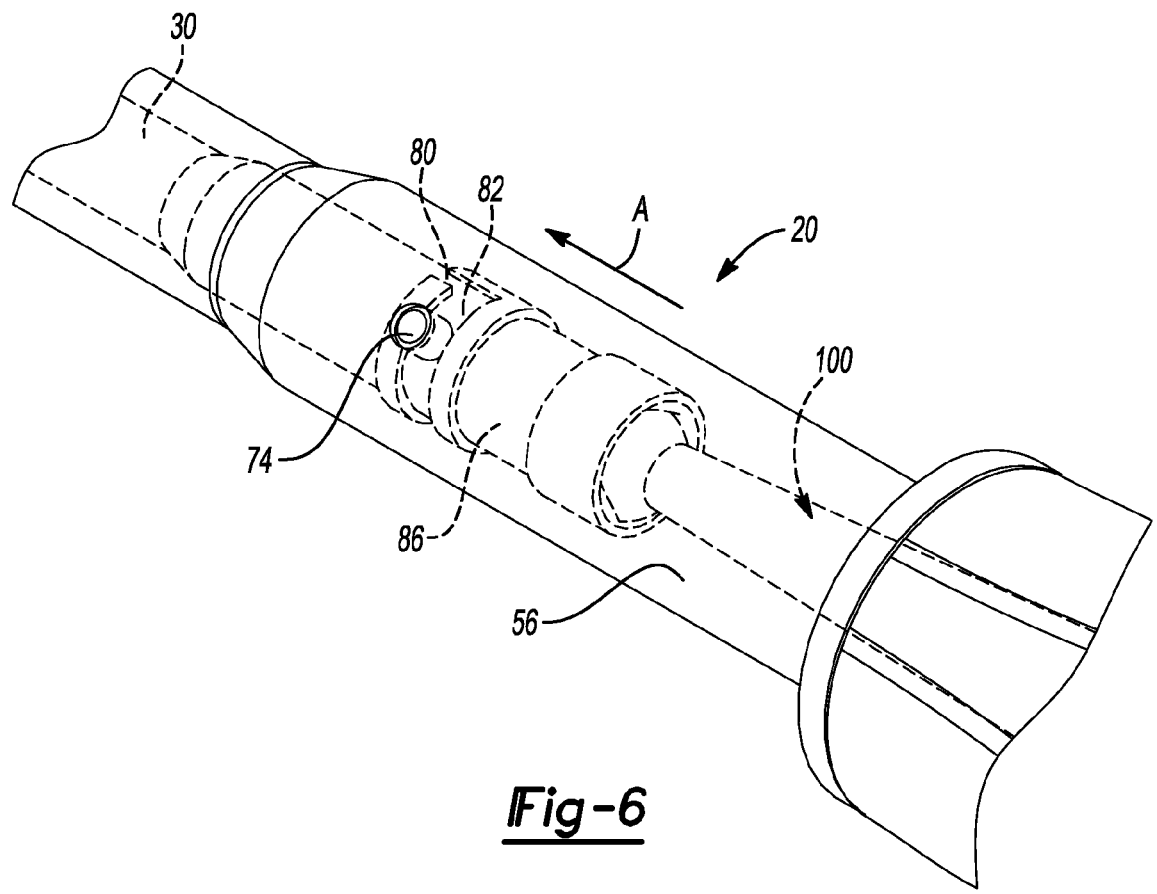
FIG. 6 is a detailed perspective phantom view of the insertion assembly of FIG. 1.
Figure 7:
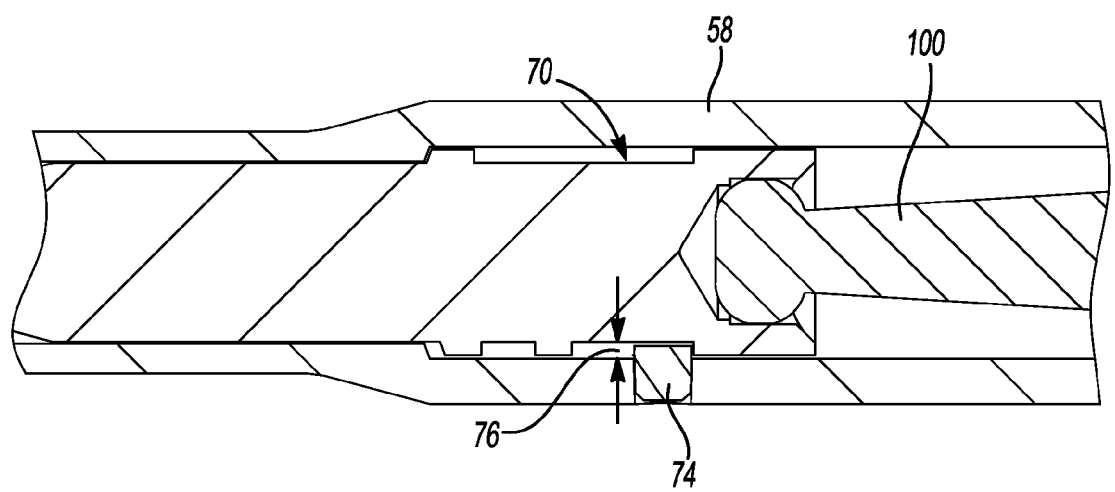
FIG. 7 is a detailed cross-sectional view of the insertion assembly of FIG. 1.

With continuing reference to FIGS. 1-4B and additional reference to FIGS. 5, 6, and 7, the threaded rod 30 can be positioned into the handle member 22 by insertion into the cannula 56, such as through an opening 105. The projection member 74 can engage the first opening 80 and pass there through. The projection member 74 can engage or move through the opening 80 by rotating the threaded rod 30, such as with the driving tool 100, to align the opening 80 with the projection 74.

While continuing to move the threaded rod 30 generally in the direction of Arrow A, the insertion or driving instrument 100 can be used to rotate the threaded rod 30 to move the threaded rod 30 relative to the projection member 74 such that the projection member 74 rides or moves within the semicircumferential passage 82. After a selected amount of rotation, such as a one-quarter (e.g. about 90 degrees of rotation) to about three-quarters (e.g. about 270 degrees of rotation), including about one-half rotation (e.g. about 180 degrees of rotation) of the threaded rod 30, the projection member 74 can be aligned with the second opening 84. The driving member 100 can apply axial force and rotation motion substantially simultaneously, thus, when the projection 74 is aligned with the opening 84 the projection 74 will move through the opening 84 and into the complete circumferential groove or passage 86. The interactions of the projection 74 and the slot portion 70 are illustrated generally in 4A-7.

Once the projection member 74 is within the complete circumferential passage 86, the threaded rod can be rotated 360° around its axis while it is within the cannula 56 of the handle member 22. When the threaded rod 30 is rotated relative to the handle member 22, the threaded end or thread 36 of the rod 30 can be threaded into the threaded bore 42 of the acetabular prosthesis 40. The threaded rod 30 is generally rotated within the cannula 56 of the handle member 22 with the driver 100. The driver 100 can be manipulated from an exterior of the handle member 22 through an opening 105 in the handle member 22, as illustrated in FIG. 5.

As the threaded rod 30 is threaded into the acetabular prosthesis 40, the acetabular prosthesis can be moved in the direction of Arrow B towards the shaped end or prosthesis engaging end 26 of the handle member 22. As the prosthesis engaging end 26 includes at least a flat side or a keyed portion 112, the acetabular prosthesis 40 can include a complementary depression or passage 110 to engage or interact with a flat or keyed portion 112 of the prosthesis engaging end 26 of the handle member 22. The rotation of the threaded rod 30 and the interaction of the threads 36 of the threaded rod 30 and the threaded bore 42 of the acetabular prosthesis 40 can interact to move the acetabular prosthesis 40 into a tight and fixed engagement relative to the keyed portion 112 of the handle member 22. Accordingly, the acetabular prosthesis 40 can be rotationally fixed relative to the handle member 22 due to the interaction and complementary configuration of the acetabular prosthesis 40 keyed depression 110 and the handle member keyed portion 112. Additionally, due to the threaded engagement of the threaded rod 30 with the acetabular prosthesis 40 and the positioning of the shoulder 60 within the cannula 56 of the handle member 22 and the complementary shoulder 66 of the threaded rod 30, the acetabular prosthesis 40 is also substantially axially fixed relative to the handle member 22. The projection 74 within the continuous or circumferential groove 86 assists in holding the threaded rod 30 within the handle member 22.

Figure 8:
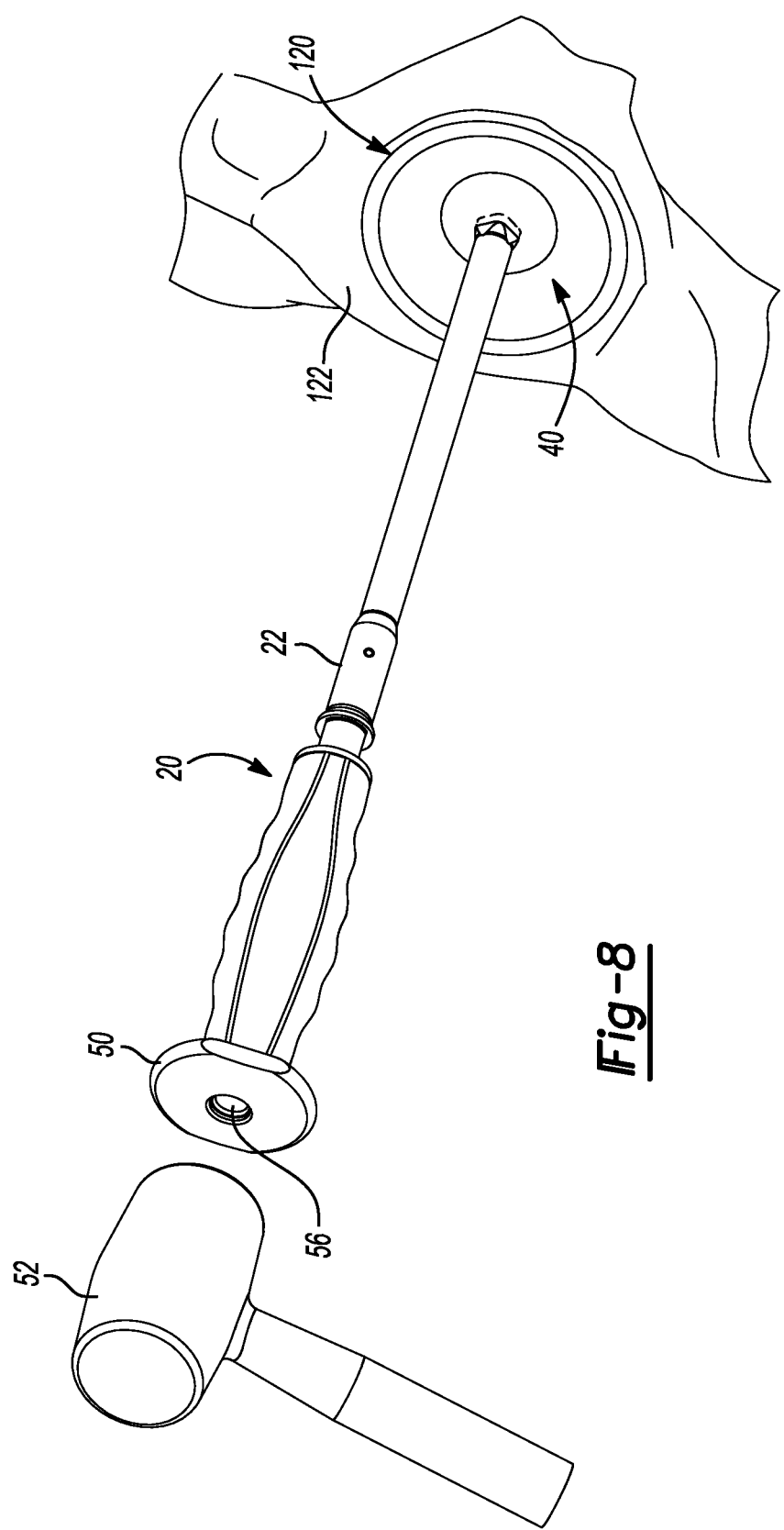
FIG. 8 is an environmental view of the insertion assembly and an attached acetabular prosthesis.

Due to the connection of the acetabular prosthesis 40 with the handle member 22 and the threaded rod 30, a user can control both position and version (i.e., rotational control) of the acetabular prosthesis 40 during an implantation procedure. As illustrated in FIG. 8, the acetabular prosthesis 40 can be positioned into a prepared acetabulum 120 of a pelvis 122. The pelvis 122 can be in appropriate subject, such as a human subject. The mallet 52 can be used to impact the acetabular prosthesis 4 through the insertion assembly 20, including the handle member 22. Again, the handle member 22 is substantially in direct contact with the acetabular prosthesis 40 due to the connection of the threaded rod 30 and the handle member 22, as discussed above. Accordingly, the impaction from the mallet 52 is directed substantially through the handle member 22 onto and into the acetabular prosthesis 40 to drive the acetabular prosthesis 40 into the prepared acetabulum 120.

Once the acetabular prosthesis 40 is properly or selectively positioned within the acetabulum 120, the insertion assembly 20 can be removed from the acetabular prosthesis 40. Substantially in reverse of the connection process discussed above, the driving tool 100 can be passed through the cannula 56 to engage the threaded rod 30 at the tool engaging region 96 to unthread the threaded rod 30 from the acetabular prosthesis 40. Once the threaded rod 30 is disengaged from the acetabular prosthesis 40, the insertion assembly 20 can be removed from the acetabular prosthesis 40 as a single unit as the threaded rod 30 is captured within the insertion handle member 20 by the projection 74 in the substantially continuous groove or passage 86.

Once removed from the acetabular prosthesis 40, the insertion assembly 20 can then be disassembled for cleaning. The insertion assembly 20 can be disassembled into substantially two components by moving the threaded rod 30 such that the projection 74 passes first through the second opening 84, is then rotated through the short groove 82, and then through the first opening 80. Once the projection is moved through the first opening 80 and generally out of the slot region 70, the threaded rod 30 can be withdrawn from the insertion handle member 22 substantially through the opening 105 near the impaction plate 50. Accordingly, the two members, including the handle member 22 and the substantially solid threaded rod 30, can be cleaned in an appropriate manner, such as with a cleaning solution and/or an autoclave or similar heat sterilization or chemical sterilization system.

Figure 9A:
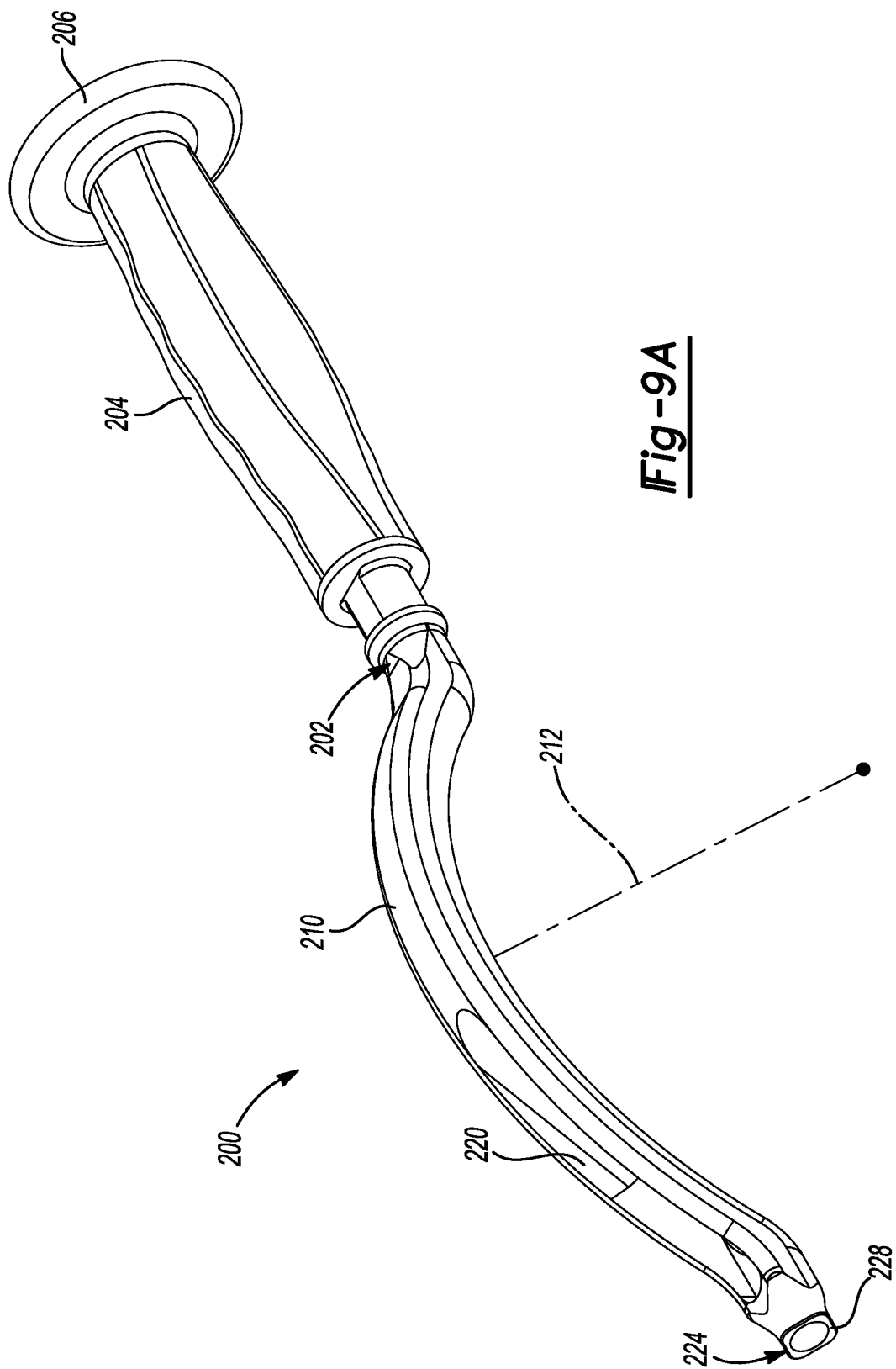
FIG. 9A is a perspective view of a portion of an insertion assembly according to various embodiments.
Figure 9B:
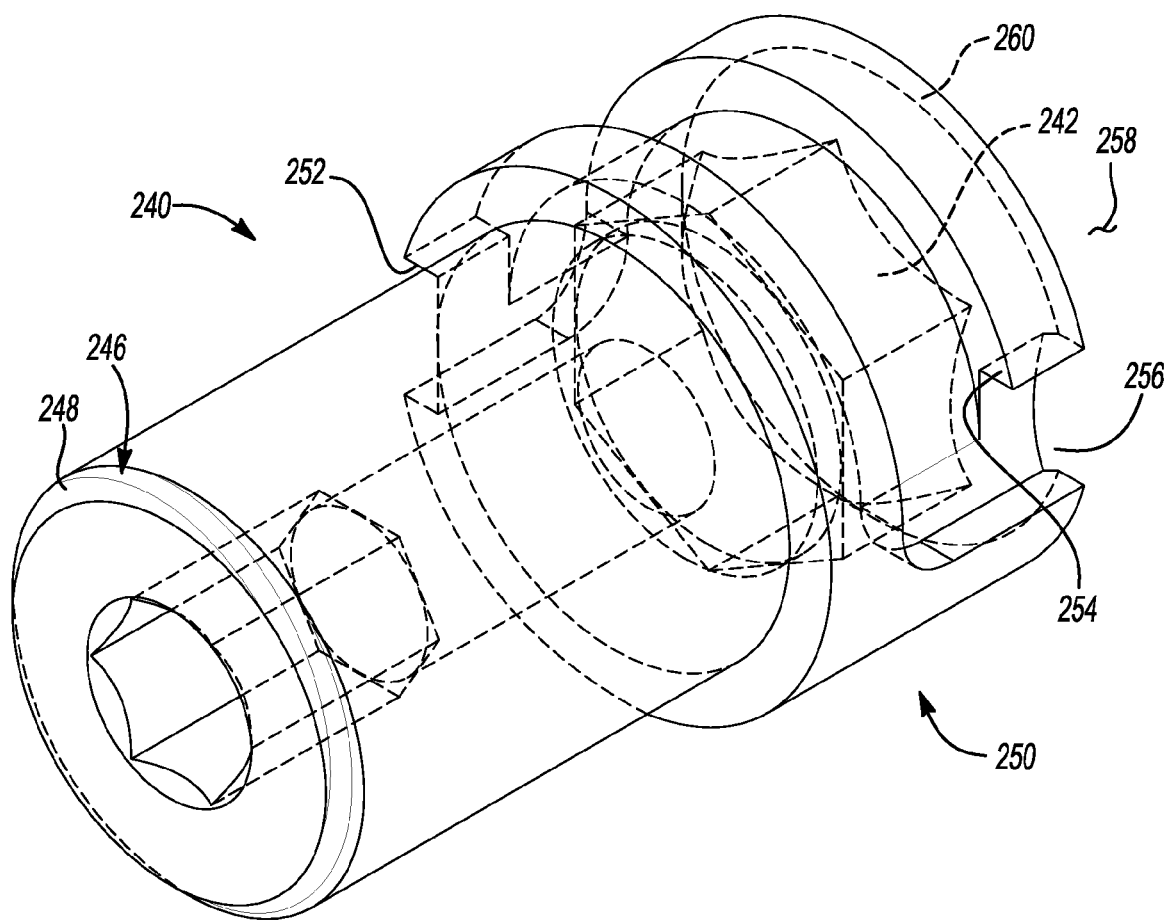
FIG. 9B is a perspective view of a portion of an insertion assembly according to various embodiments.
Figure 10:
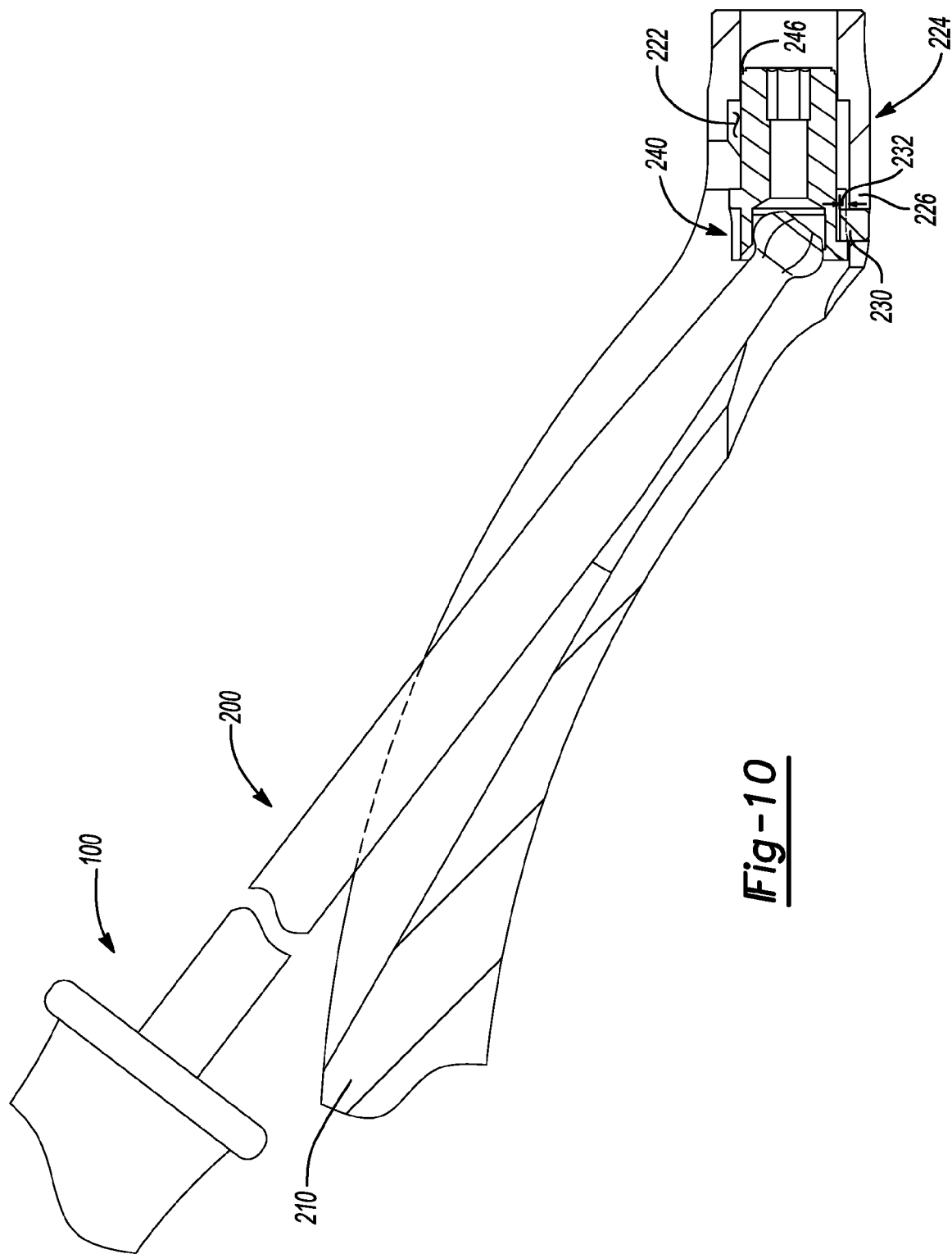
FIG. 10 is a detailed cross-sectional view of the insertion assembly of FIG. 9.

According to various embodiment, as illustrated in FIGS. 9 and 10, an insertion assembly 200 is illustrated. The insertion assembly 200 can include portions that are similar to that illustrated and discussed relative to the insertion assembly 20 above. Those portions that are substantially similar will be discussed only briefly here. For example, the insertion assembly 200 can include a handle member 202 that includes a graspable region or portion 204 similar to the graspable region 24 discussed above. An impaction plate 206 can also be provided at an end of the handle member 202.

The handle member 202 can include an arcuate portion or member 210. The arcuate member 210 can be an extended or prosthesis engaging portion or member that is defined by a curve or an arc having a radius 212. The arcuate member 210 can assist in allowing for placement of the acetabular prosthesis 40 substantially around a minimally dislocated femur to allow for a less invasive procedure, including less disruption of soft tissue and a smaller incision. The arcuate member 210 can define a cannula 222 along a selected length of the arcuate member 210. A depression or groove 220 can be defined through at least a portion of the arcuate member 210. The groove 220 can extend to the cannula or through-bore 222 defined through an end 224 of a wall 226 of the arcuate member 210. Near the end 224 can be a prosthesis engaging keyed surface 228 that can have a substantially keyed or non-circular configuration similar to the end 26 of the insertion assembly 20, discussed above.

A projection 230 can extend a distance 232 into the cannula 222 similar to the projection 74, discussed above. A threaded rod 240, as illustrated in FIG. 10, can be positioned in the cannula 222 and manipulated substantially similarly to the threaded rod 30 discussed above. The threaded rod 240, however, can include a length that is shorter than the threaded rod 30 discussed above to fit within the cannula 222 and allow the driving instrument 100 to engage a tool engaging end 242 through the groove 220.

The threaded rod 240 can include a threaded end 246 that includes threads 248 similar to the thread of the threaded rod 30 discussed above. The threads 248 can be manipulated to engage the prosthesis 40. As discussed above, rotating the threaded rod 240 to engage the acetabular prosthesis 40 can move the prosthesis 40 to engage the end 224 of the handle member 22.

The threaded rod 240 can also include a slot region 250 similar, or even identical, to the slot region 70 of the threaded rod 30, discussed above. The slot region 250 can include a first slot opening 252 through which the projection member 230 can pass into a semi-circumferential passage or short groove 254. The threaded rod 240 can then be rotated until the projection member 230 is able to pass through a second opening 256.

Once the projection member 230 is through the second opening 256, the threaded rod 240 can be moved relative to the projection member 230 to allow the projection member 230 to pass into an uninterrupted area 258 that is an area of clearance that is opposite the threaded end 246. The area of clearance 258 can be defined beyond a first wall 260 of the threaded rod 240 that is opposite the threaded end 246. The area of clearance 258 can be considered a complete path or long groove that allows rotation of the threaded rod 240. Accordingly, once the projection member 230 is beyond the end wall 260 and in the area of clearance 258, the threaded rod 240 can be rotated 360° at least one time, and generally a plurality of times, to turn the threads 248 to engage the threaded bore 42 of the prosthesis 40.

By rotating the threaded rod 240, the threaded rod 240 can be engaged and disengaged from the prosthesis 40 similar to the process of the threaded rod 30, discussed above. The insertion assembly 200 can, therefore, be operated substantially similar to the insertion assembly 20 discussed above save for the configuration of the arcuate portion 210 and the shortened length of the threaded rod 240 due to the positioning of the cannula 222 substantially only at an end of the arcuate member 210.

Accordingly, the insertion assemblies 20, 200 can be used to insert the acetabular prosthesis 40, or any appropriate member or prosthesis, while having substantially both axial positional control and version (i.e., rotational) control of the acetabular prosthesis 40. While having at least the two degrees of freedom of control of the acetabular prosthesis 40, the acetabular prosthesis 40 can be substantially precisely positioned within the prepared acetabulum 120 of the pelvis 122. It is understood that a procedure can further include removing the insertion assemblies 20, 200, as discussed above, and positioning a liner within the acetabular prosthesis 40, reducing a femur into the acetabular prosthesis 40, either with a natural femoral head or a femoral prosthesis member, or any other appropriate procedure step. Regardless, the insertion assemblies 20, 200 can include substantially two components that can be efficiently disassembled for ease of cleaning and efficiently assembled for engagement of an acetabular prosthesis in both rotational and axial position control.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system to implant a prosthesis into a subject, comprising:
   a handle member extending from a handle first end to a handle second end and defining a bore through at least a portion of the handle member, and defining a longitudinal axis along the bore of the handle;
   a threaded member configured to pass coaxially into the through bore, the threaded member extending from a member first end to a member second end, the threaded member having threads formed at the member first end to threadably engage the prosthesis and a slotted region at the member second end, the slotted region including a slot formed in an outer surface of the threaded member which does not extend into the threads, the slotted region for coupling the threaded member to the handle member; and a projection extending into the bore formed in the handle member configured to engage the slot to hold the threaded member in the handle member;

wherein the threaded member slotted region slot includes a first slot portion shaped to engage with the projection to hold the threaded member in the handle member at a position substantially axially fixed on the longitudinal axis, and wherein the threaded member includes a second slot portion adjacent to but separated from the first slot portion wherein the second slot portion includes an uninterrupted area configured to allow axial advancement of the threaded member along the longitudinal axis to engage the threads with the prosthesis when the threaded member is coupled to the handle member, and wherein the first slot portion is configured to limit a rotation of the threaded member within the handle about the longitudinal axis when the threaded member is coupled to the handle member.

2. The system of claim 1, further comprising:
the prosthesis, and
a driving member configured to rotate the threaded member about a long axis of the threaded member to both engage the threaded member within the bore of the handle member and rotate the threaded member to threadably engage the prosthesis.

3. The system of claim 2, wherein the first slot portion is discontinuous about the threaded member and includes a double "J" shape slot configuration.

4. The system of claim 2, wherein the first slot portion includes a first opening through a first wall defining a walled groove and a second opening through a second wall defining the walled groove;
wherein the first wall is spaced apart from the second wall along the longitudinal axis and the first wall is nearer the threaded end than the second wall, and
wherein manipulation of the threaded member relative to the projection to navigate the projection through the second opening moves the projection into the second portion of the threaded member to facilitate axial advancement of the threaded member to engage the threads on the implantable prosthesis, and navigation of the projection through the first opening facilitates disassembly of the threaded member from the handle member.

5. The system of claim 1, wherein the handle first end has an external surface that is keyed to the prosthesis to at least resist rotation of the prosthesis relative to the longitudinal axis of the handle member.

6. The system of claim 1, wherein the handle member has an internal wall defining the bore, wherein the bore has a first region with a first diameter less than a second diameter of a second region, and the internal wall defines a shoulder between the first region and the second region;
wherein the shoulder is configured to engage the threaded member to stop the threaded member from passing entirely through the handle member.

7. The system of claim 1, wherein the handle member defines the bore through an entire length of the handle member from the handle first end to the handle second end.

8. The system of claim 1, wherein the second slot portion is an uninterrupted circumferential groove that extends around the threaded member.

9. The system of claim 1, wherein the second slot portion abuts an end wall of the threaded member.

10. A system to implant a prosthesis into a subject, comprising:
a handle member extending from a handle first end to a handle second end and defining a bore through at least a portion of the handle member;
a threaded member extending from a member first end to a member second end, the threaded member configured to be inserted coaxially into the bore, the threaded member including:
a thread formed at the member first end to threadably engage the prosthesis, and
a slotted region at the member second end including a slot formed into an outer surface of the threaded member, the slot not extending into the threaded region, the slot including a first slot portion that is discontinuous about the threaded member formed by at least a first slot wall and a second slot wall, wherein a first opening is formed through the first slot wall and a second opening is formed through the second slot wall with an interrupted groove defined between the first slot wall and the second slot wall extending a part of a distance around the threaded member between the first opening and the second opening and a second portion that includes an uninterrupted region that is configured to allow complete rotation of the threaded member relative to the handle member when the threaded member is coupled to the handle member; and
a projection member extending into the bore formed in the handle member configured to engage the slot to hold the threaded member in the handle member;
wherein the projection is operable to engage both the first slot portion that is discontinuous to limit a rotation of the threaded member within the handle member and the second slot portion to allow a complete rotation of the threaded member within the handle member.

11. The system of claim 10, further comprising:
a driving member configured to rotate the threaded member about a long axis of the threaded member to both engage the threaded member within the bore of the handle member and rotate the threaded member to threadably engage the prosthesis.

12. The system of claim 11, wherein the first slot portion that is discontinuous about the threaded member includes a double "J" shape configuration defined by at least the first slot wall, the second slot wall, and the interrupted groove.

13. The system of claim 10, wherein the handle first end has an external surface that is keyed to the prosthesis to at least resist rotation of the prosthesis relative to the handle member;
wherein rotating the threaded member about a long axis of the threaded member draws the prosthesis towards the keyed external surface.

14. The system of claim 10, wherein the handle member has an internal wall defining the bore, wherein the bore has a first region with a first diameter less than a second diameter of a second region, and the internal wall defines a shoulder between the first region and the second region;
wherein the shoulder is configured to engage the threaded member to stop the threaded member from passing entirely through the handle member.

15. The system to claim 10, wherein the handle member defines the bore through the entire length of the handle member.

16. The system to claim 11, wherein the handle member includes a curved portion and a substantially straight portion, wherein the bore extends substantially only in the substantially straight member;
wherein the driving member engages the threaded member within the bore.

17. The system of claim 16, wherein the curved portion defines a groove;
wherein the driving member engages the threaded rod in the bore through the groove formed in the curved portion.

18. The system of claim 10, wherein the second slot portion is an uninterrupted circumferential groove that extends around the threaded member.

19. The system of claim 10, wherein the second slot portion includes an uninterrupted area beyond an end wall of the threaded member.

20. A method of implanting a prosthesis into a subject, comprising:
providing a handle member extending from a first handle end to a second handle end and having a bore through at least a portion of the handle member, the handle member defining a longitudinal axis from the first handle end to the second handle end;
providing a threaded member extending from a first threaded member end to a second threaded member end for positioning coaxially into the bore, wherein the threaded member includes:
a thread formed at the first threaded member end configured to threadably engage the prosthesis, and
a slotted region formed at the second threaded member end including a slot formed into an outer surface of the threaded member, the slot not passing into the thread, the slot including a first slot portion that is discontinuous about the threaded member formed by at least a first slot wall and a second slot wall, wherein a first opening is formed through the first slot wall and a second opening is formed through the second slot wall with an interrupted groove defined between the first slot wall and the second slot wall extending at least a part of a distance around the threaded member between the first opening and the second opening, and the slot including a second slot portion that includes an uninterrupted region defined relative to the threaded member; and
providing a projection member extending into the bore to engage the slot to hold the threaded member in the handle member;
wherein the projection is operable to engage the first slot portion within the handle member to limit a rotation of the threaded member within the handle about the longitudinal axis, and wherein the projection is configured to engage the second slot portion to allow a complete rotation of the threaded member within the handle member about the longitudinal axis.

21. The method of claim 20, further comprising:
forming the bore through the entire length of the handle member from the first handle end to the second handle end.

22. The method of claim 20, wherein providing a projection member, includes:
forming a passage through a wall of the handle member into the bore; positioning the projection member through the passage through the wall; and fixing the projection member to the wall to extend a selected distance into the bore of the handle member.

23. The method of claim 20, further comprising:
providing a driving member to engage the threaded member within bore to rotate the threaded member about the longitudinal axis.

24. The method of claim 23, further comprising:
passing the threaded member into the bore;
aligning the first opening with the projection member;
moving the threaded member to move the projection member into the interrupted groove;
rotating the threaded member relative to the handle member while the projection member is within the interrupted groove to align the second opening with the projection member; and
axially moving the threaded member to move the projection member through the second opening and into the uninterrupted region, wherein the uninterrupted region includes an uninterrupted groove defined by the threaded member.

25. The method of claim 24, further comprising:
engaging the threaded member with the driving member;
wherein the threaded member is rotated and moved axially relative to the driving member.

26. The method of claim 24, further comprising:
rotating the threaded member while the projection member is in the uninterrupted groove to thread the thread into the prosthesis to fix the prosthesis against an end of the handle member to axially and rotationally fix the prosthesis relative to the handle member.

27. A system comprising:
an implantable prosthesis;
a handle member extending from a handle proximal end to a handle distal end and defining a bore which extends at least partially through at least a portion of the handle member and defines a longitudinal axis along the bore of the handle;
a threaded member configured to pass coaxially into the bore, the threaded member extending from a member proximal end to a member distal end,
the threaded member having threads formed at the member distal end to threadably engage the implantable prosthesis; and
the threaded member having an outer surface and at least one wall extending radially outwardly from the outer surface, the at least one wall extending around the outer surface of the threaded member, the threaded member further having portions defining a proximate wall opening and a distal wall opening,
a projection coupled to the handle member and extending into the bore formed in the handle member, the projection sized and shaped to engage the at least one wall to retain the threaded member in the handle member at a position substantially axially fixed on the longitudinal axis,
wherein the proximate wall opening is configured to allow the projection to pass through the proximate wall opening to enable distal axial advancement of the threaded member relative to the handle along the longitudinal axis to engage threads on the prosthesis, and the distal wall opening in the at least one wall is configured to allow the projection to pass through the distal wall opening to enable proximal axial movement of the threaded member relative to the handle member.

* * * * *